US00PP25575P3

(12) United States Plant Patent
Trigiano et al.

(10) Patent No.: US PP25,575 P3
(45) Date of Patent: May 26, 2015

(54) ***CORNUS KOUSA* TREE NAMED 'PAM'S MOUNTAIN BOUQUET'**

(50) Latin Name: *Cornus kousa*
Varietal Denomination: Pam's mountain bouquet

(75) Inventors: Robert N. Trigiano, Maryville, TN (US); Phillip A. Wadl, Powell, TN (US); Mark T. Windham, Knoxville, TN (US); Richard M. Evans, Oak Ridge, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 165 days.

(21) Appl. No.: 13/506,624

(22) Filed: May 3, 2012

(65) Prior Publication Data

US 2013/0298297 P1 Nov. 7, 2013

(51) Int. Cl.
*A01H 5/02* (2006.01)

(52) U.S. Cl.
CPC ..... *A01H 5/02* (2013.01)
USPC ..... Plt./220

(58) Field of Classification Search
USPC ..... Plt./220
See application file for complete search history.

(56) References Cited

PUBLICATIONS

Wadl, P.A. et al. "Microsatellites from kousa dogwood (*Cornus kousa*)" *Molecular Ecology Resources,* 2008, pp. 780-782, vol. 8.
Wadl, P.A. et al. "Molecular Identification Keys for Cultivars and Lines of *Cornus florida* and *C. kousa* Based on Simple Sequence Repeat Loci" *Journal of the American Society for Horticultural Science,* 2008, pp. 783-793, vol. 133, No. 6.

*Primary Examiner* — Anne Marie Grunberg
(74) *Attorney, Agent, or Firm* — Saliwanchik, Lloyd & Eisenschenk

(57) ABSTRACT

A new and distinct cultivar of flowering dogwood tree, which has fused bracts is provided. This dogwood tree is botanically known as *Cornus kousa* and referred to by the following cultivar name: 'Pam's Mountain Bouquet'.

3 Drawing Sheets

BACKGROUND OF THE INVENTION

The present invention relates to a new and distinct cultivar of flowering dogwood tree cultivar, which has fused bracts. This dogwood tree is botanically known as *Cornus kousa* and hereinafter referred to by the following cultivar name: 'Pam's Mountain Bouquet'.

This new dogwood cultivar was discovered in a planting of seedlings within a cultivated area in Oak Ridge, Tenn. 'Pam's Mountain Bouquet' is a selection from the original seedlings grown in Oak Ridge, Tenn. from seed gifted by Polly Hill. Asexual reproduction of 'Pam's Mountain Bouquet' by rooting of harvested terminal cuttings and grafting of axillary buds onto seedling rootstocks in Oak Ridge, Tenn. and at a nursery located in Belvidere Tenn. have shown that the unique features of this new dogwood cultivar are stable and reproduced true-to-type in successive vegetative generations.

DETAILED DESCRIPTION OF THE NEW VARIETY

Figure 1:
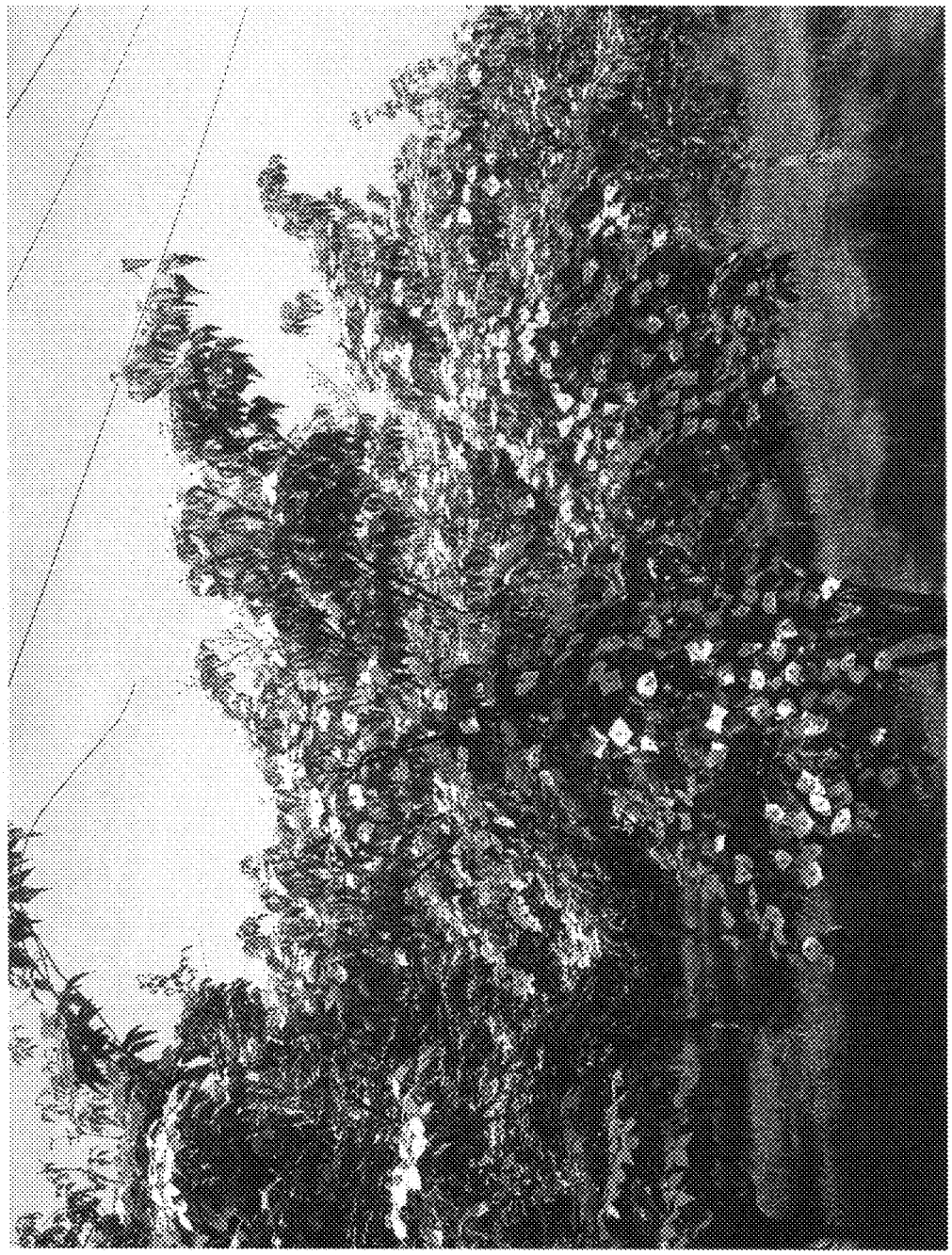
FIG. 1. Photograph of 'Pam's Mountain Bouquet'. Colors in the photograph may differ from actual colors due to lighting and light reflectance.

A new and distinct cultivar of flowering dogwood tree cultivar, which has fused bracts is provided. This dogwood tree cultivar is botanically known as *Cornus kousa* and referred to by the following cultivar name: 'Pam's Mountain Bouquet'. This cultivar appears to be resistant to powdery mildew caused by *Erisphe pulchra* and dogwood anthracnose caused by *Discula destructiva.*

This new and distinct dogwood tree cultivar was discovered in a planting of seedlings within a cultivated area in Oak Ridge, Tenn. and arose from seed gifted by Ms. Polly Hill. 'Pam's Mountain Bouquet' is a selection from the original seedlings. The instant cultivar was derived from open-pollinated seeds that were bulked from maternal parents 'Big Apple', 'Snowbird', 'Steeple' and an unnamed tree and the potential paternal parents 'Big Apple', 'Julian', 'Steeple' and another unnamed tree (Auge et al., 2002). Thus, it is not possible to ascertain the exact parentage. The subject dogwood tree cultivar differs from all of the potential parents in that the instant cultivar has fused bracts, whereas none of the potential parent cultivars show the same characteristic.

Asexual reproduction of 'Pam's Mountain Bouquet' by rooting of harvested terminal cuttings and grafting of axillary buds onto seedling rootstocks in Oak Ridge, Tenn. and at a nursery located in Belvidere, Tenn. has shown that the unique features of this new dogwood cultivar are stable and reproduced true-to-type in successive generations.

DETAILED BOTANICAL DESCRIPTION

The following observations, measurements and comparisons describe this cultivar grown in Oak Ridge, Tenn. Trees used for this description were about twenty (20) years old. Plant hardiness is expected to be zones 4-9. The color characteristic descriptions use color references to The Royal Horticultural Society (R.H.S.) Colour Chart (published 2001), except where general terms of ordinary dictionary significance are used. Measurements are provided as an average (with ranges also provided as indicated).

The following Table 1 shows microsatellite (SSR) markers used to perform unweighted pair group with arithmetic mean (UPGMA) cluster analysis of 29 cultivars and lines of *Cornus kousa*. GenBank accession numbers are given along with, locus designations, forward (F) and reverse (R) primer sequences (5'-3' direction), and repeat motif:

TABLE 1

| GenBank accession no. | Locus | Primer sequences (5'-3') | Repeat |
|---|---|---|---|
| EU544308 | CK005 | F:GCATTTGTCCTTTGTTTGACAT (SEQ ID NO: 1)<br>R:TTTTTCGCGAAGTGTTCTCTAC (SEQ ID NO: 2) | $(AC)_{20}$ |
| EU125522 | CK007 | F:GAGCCCAGAAGAAGAATATAGAC (SEQ ID NO: 3)<br>R:ATATAATTGGGTTGGGTTTTG (SEQ ID NO: 4) | $(AG)_{8}$ |
| EU125523 | CK015 | F:GTCAAATTTTTGATCTTTCTCTCT (SEQ ID NO: 5)<br>R:GGAGAGACAGAGTACAGTAGAGGT (SEQ ID NO: 6) | $(CT)_{10}$ |
| EU125524 | CK029 | F:AATTTAGGTTAAGGTTTTGATTTG (SEQ ID NO: 7)<br>R:AGAGAGAATAGGTTACAGCATCAT (SEQ ID NO: 8) | $(TC)_{8}$ |
| EU125525 | CK031 | F:TGTCACTGCTTACAGAAACAAT (SEQ ID NO: 9)<br>R:TATGACGAGATTGTATAAGTTGCT (SEQ ID NO:10) | $(CT)_{7}$ |
| EU125526 | CK040 | F:CCAAGTCAGTTTGGTAGTAATTC (SEQ ID NO: 11)<br>R:AGTGCAACTTTTACTTGCTATGT (SEQ ID NO: 12) | $(GT)_{16}$ |
| EU125529 | CK048 | F:ACCAACCAAAAGAAGTATAAAGAA (SEQ ID NO: 13)<br>R:CCTATAAATAAGGAGTGATTTGGT (SEQ ID NO: 14) | $(TA)_{6}$ |
| EU544309 | CK058 | F:CTTAAGTCACAAAGACAATGAAAT (SEQ ID NO: 15)<br>R:AAGAGAGTTCAGATTTATCTTTGC (SEQ ID NO: 16) | $(GT)_{10}$ |
| EU544310 | CK070 | F:CTTTTCTACACCCTTAACAAGTG (SEQ ID NO: 17)<br>R:TAGACAATATGTGCTTAATTGGTT (SEQ ID NO: 18) | $(GT)_{9}$ |

TABLE 1-continued

| GenBank accession no. | Locus | Primer sequences (5'-3') | Repeat |
|---|---|---|---|
| EU544311 | CK071 | F:CTGCTCGGTTAAGGTATGTT (SEQ ID NO: 19)<br>R:TTTAAAGTGCGTTGTATACATAAAT (SEQ ID NO: 20) | $(TG)_{9}$ |
| EU544312 | CK072 | F:AGCACTCATAGTCCTTGCAC (SEQ ID NO: 21)<br>R:GTTAAAACGAAGAAGATACAACAA (SEQ ID NO: 22) | $(GT)_{10}$ |

TABLE 2

Characteristics of Pam's Mountain Bouquet'
Color Descriptions are based upon the
Royal Horticultural Society's (RHS) colour chart, 2001.

| | Character | Generalized Characteristics | 'Pam's Mountain Bouquet' | Comparative Variety (Milky Way Select) |
|---|---|---|---|---|
| 1 | Tree form (observation) | upright<br>semi-upright<br>spreading<br>weeping<br>others | spreading | Spreading-to semi-upright |
| 2 | Tree height (observation) | dwarf<br>low<br>medium<br>high<br>very high | low (about 3-4 meters; spread about 4 -5 meters, and dependent on age and environment) | Medium |
| 3 | Branch thickness (measurement) Thickness in the middle portion of a plant | thin<br>medium<br>thick | medium (age dependent) | Medium |
| 4 | Color of current Shoot (observation) current shoot color in the middle portion of a plant | Yellow<br>Yellow green<br>Green<br>Grayish green<br>Purple<br>Crimson<br>Brown<br>Others | Green 143B | Green 143B |
| 5 | Branch color (observation) current branch color in the middle portion of a plant second year+ | Yellow<br>Yellow green<br>Green<br>Purplish crimson<br>Crimson<br>Brown<br>Others | Greyed; Green 198B | Greyed; Green 198B |
| 6 | Dark spots on Branch (observation) presence of dark spots on the branch | Absent<br>Present | Absent | Absent |
| 7 | Branching (observation) density of branching | Low<br>Medium<br>High | High | Medium |
| 8 | Internode length (measurement) Internode length in the middle portion of a plant | Short<br>medium<br>long | Short | Short |

TABLE 2-continued

Characteristics of Pam's Mountain Bouquet'
Color Descriptions are based upon the
Royal Horticultural Society's (RHS) colour chart, 2001.

Figure 2B:
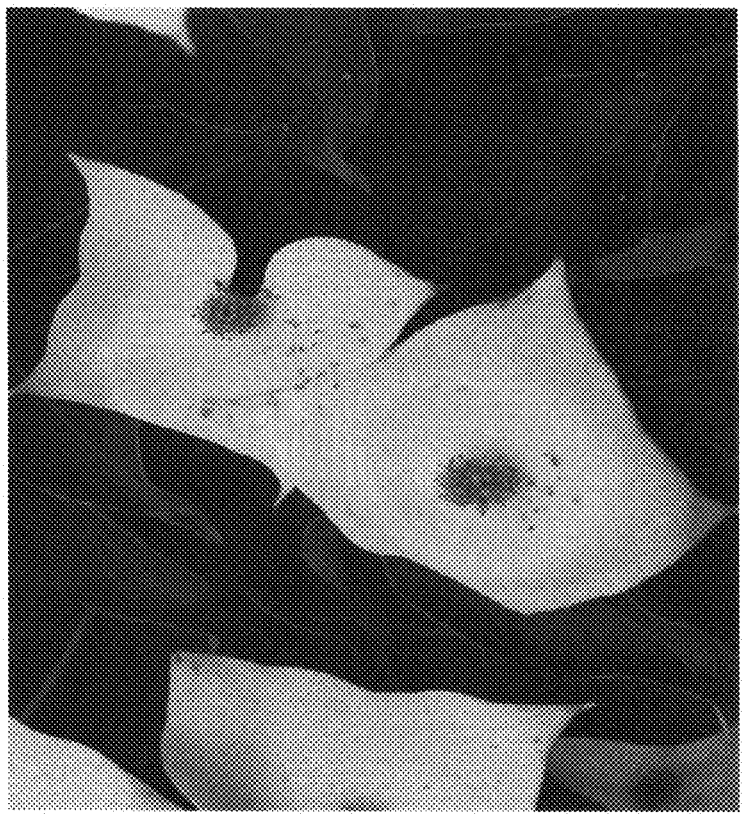
FIGS. 2A and 2B. Close-up Photographs of 'Pam's Mountain Bouquet' bracts.
Figure 2A:
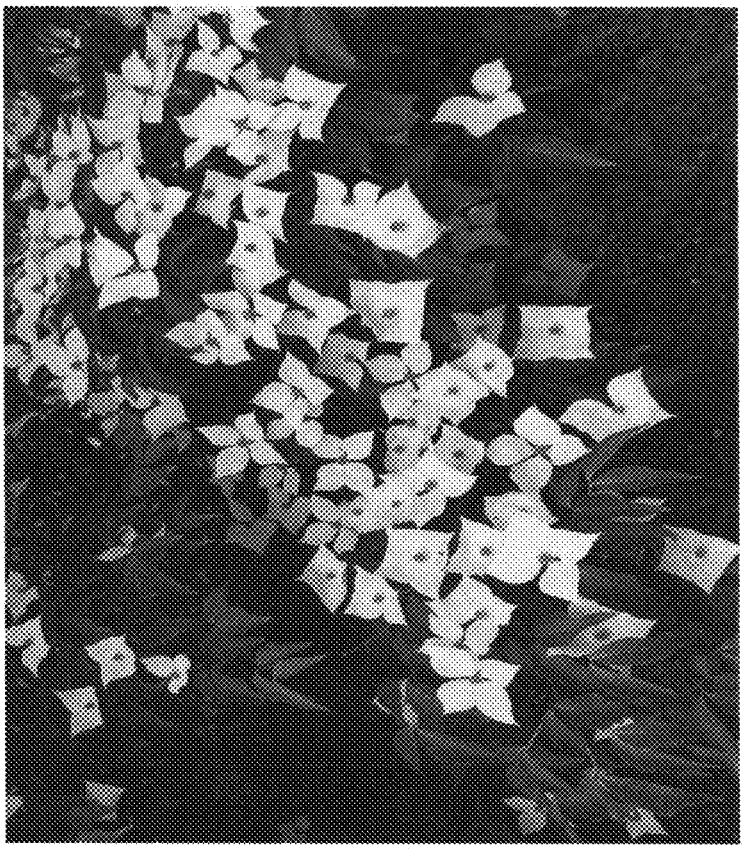
Figure 3:
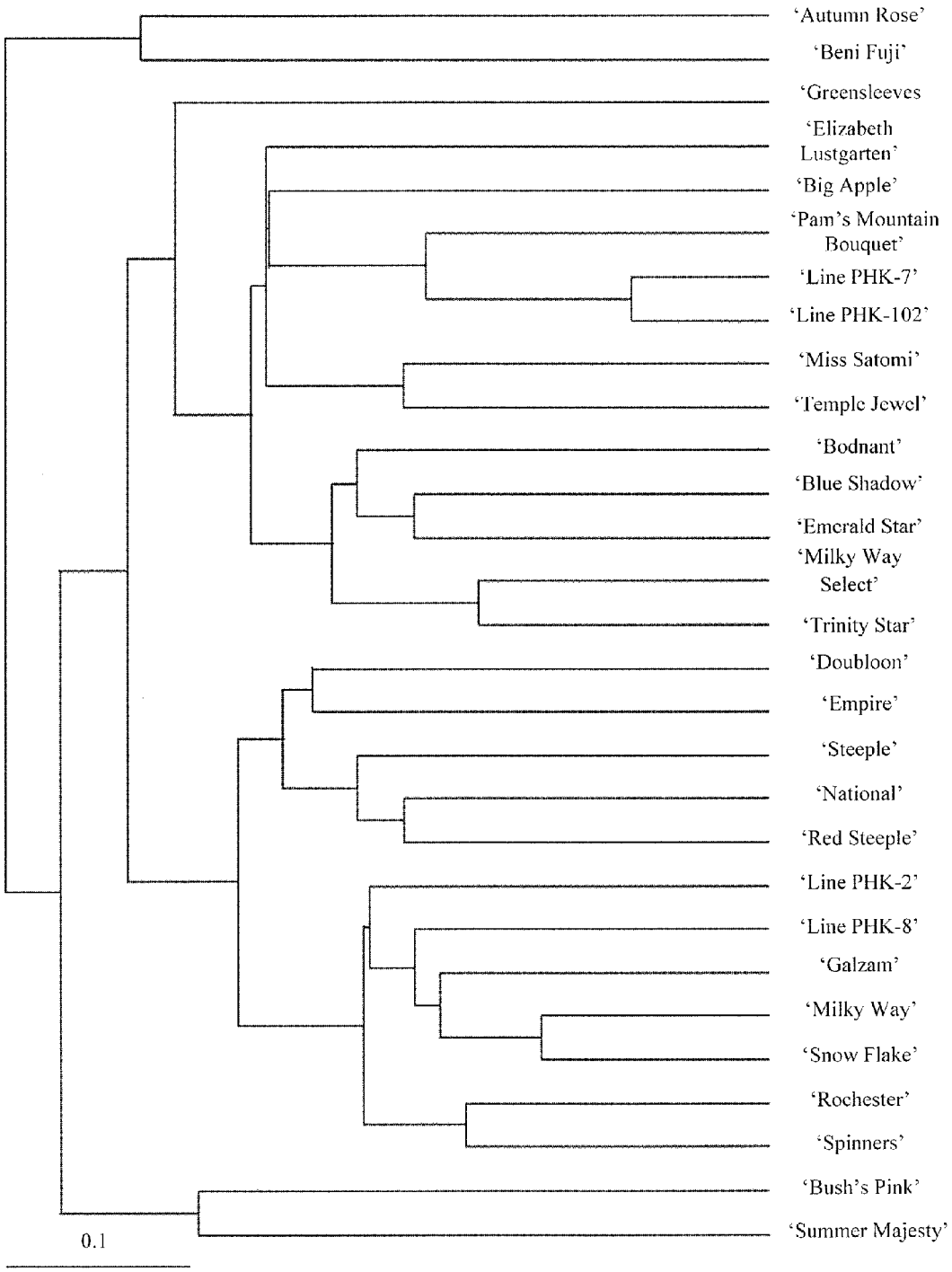
FIG. 3. Dendrogram illustrating the relatedness of "Pam's Mountain Bouquet" to other selected *Cornus kousa* cultivars using 11 microsatellite (SSR; Simple Sequence Repeat) markers. Note: Cultivar Beni Fuji is disclosed in U.S. Plant. Pat. No. 8,676.

| | Character | Generalized Characteristics | 'Pam's Mountain Bouquet' | Comparative Variety (Milky Way Select) |
|---|---|---|---|---|
| 9 | whole shape of leaves (observation) see Fig. 1 whole shape of a leaf in the middle portion of a plant | Lanceolate<br>Oblanceolate<br>Oblong<br>Elliptical<br>Ovate<br>Obovate<br>Orbicular<br>Others | Obovate | Obovate |
| 10 | Shape of leaf tip(observation) see Fig. 2 Tip shape of a leaf in the middle portion of a plant | Acuminate<br>Acute<br>obtuse<br>Rotundate<br>Others | Acuminate | Acuminate |
| 11 | Shape of leaf Base (observation) see FIG. 2A and FIG. 2B Base shape of a leaf in the middle portion of a plant | Acuminate<br>Acute<br>obtuse<br>Rotundate<br>Others | Truncate | Truncate |
| 12 | Shape of leaf Margin (observation) shape of a leaf margin in the middle portion of a plant | Entire<br>others | Entire | Entire |
| 13 | Leaf rolling (observation) | Rolling inward<br>Flat<br>Rolling outward | Rolling inward | Rolling inward |
| 14 | Leaf curvature (observation) | In-curved<br>Flat<br>Out-curved | Flat | Flat |
| 15 | Leaf margin Undulation (observation) | None<br>presence | None | None |
| 16 | Leaf length (measurement) Length from the tip to the base of mature leaf | Short<br>Medium<br>long | Long<br>(about 10-14 cm) | Medium |
| 17 | Leaf width (measurement) The maximum width of mature leaf | Narrow<br>Medium<br>wide | Narrow<br>(about 4-5 cm) | Medium |
| 18 | Leaf thickness (observation) Thickness of mature leaf | Thin<br>Medium<br>Thick | Medium | Medium |
| 19 | Bud color (observation) Color of bud just after sprouting | Yellowish white<br>Yellow<br>Yellow green<br>Green<br>Grayish green<br>Crimson<br>Others | Grayish green<br>179A | Grayish Green<br>191A |
| 20 | Immature leaf color (observation) | Yellowish white<br>Yellow<br>Yellow green<br>Green<br>Grayish green<br>pink<br>Crimson<br>others | Light Green<br>135B | Light Green<br>135B |

TABLE 2-continued

Characteristics of Pam's Mountain Bouquet'
Color Descriptions are based upon the
Royal Horticultural Society's (RHS) colour chart, 2001.

| | Character | Generalized Characteristics | 'Pam's Mountain Bouquet' | Comparative Variety (Milky Way Select) |
|---|---|---|---|---|
| 21 | Presence of anthocyanin (observation) Coloration by anthocyanin on the immature leaf upperside | Absent<br>present | Absent | Absent |
| 22 | Color of leaf upperside (observation) Color of mature leaf upperside | Yellow<br>Yellow green<br>Green<br>Grayish green<br>Purplish crimson<br>Crimson<br>others | Green<br>143B | Green<br>146A |
| 23 | Color of leaf lowerside (observation) Color of mature leaf lowerside | Yellow<br>Yellow green<br>Light green<br>Green<br>Dark green<br>Grayish green<br>Purplish crimson<br>others | Light Green<br>146B | Medium Green<br>137A |
| 24 | Seasonal change of a mature leaf (observation) | Unchanged<br>changed | Changed | Changed |
| 25 | Color of leaves in autumn (observation) | Yellow<br>Orange<br>Crimson<br>others | Red<br>10C -46A | Dull Red to maroon<br>61B |
| 26 | Leaf variegation (observation) Variegation on leaf upperside | Not variegated<br>variegated | Not variegated | Not variegated |
| 27 | Variegation pattern (observation) Pattern of variegation on a leaf upperside | Spotted<br>Splashed<br>Margined<br>Centered<br>Blotched<br>others | NA | NA |
| 28 | Variegation color (observation) | White<br>Yellowish white<br>Greenish white<br>Yellow<br>Yellow Green<br>Green<br>Crimson<br>others | NA | NA |
| 29 | seasonal change of variegation color (observation) | Unchanged<br>changed | NA | NA |
| 30 | Hair on leaf upperside (observation) hair density on a mature leaf upperside | None<br>Low<br>Medium<br>high | None | None |
| 31 | Hair on leaf lowerside (observation) hair density on a mature leaf lowerside | None<br>Low<br>Medium<br>high | None | None |

TABLE 2-continued

Characteristics of Pam's Mountain Bouquet'
Color Descriptions are based upon the
Royal Horticultural Society's (RHS) colour chart, 2001.

| | Character | Generalized Characteristics | 'Pam's Mountain Bouquet' | Comparative Variety (Milky Way Select) |
|---|---|---|---|---|
| 32 | Petiole length (measurement) Length from the base of blade to the base petiole | Short<br>Medium<br>Long<br>Very long | Short (about 1.5-2.5 cm.) | Medium |
| 33 | Petiole width (measurement) The maximum width of a mature leaf petiole | Narrow<br>Medium<br>wide | Medium (<8 mm) | Medium |
| 34 | Petiole color (observation) | Yellowish white<br>Yellow Green<br>Green<br>Crimson<br>others | Green 143B | Green 143B |
| 35 | Inflorescence type (observation) | Corymb<br>Umbel<br>Head<br>others | Umbel | Umbel |
| 36 | Inflorescence direction (observation) | Upright<br>Horizontal<br>pendulous | Upright | Upright |
| 37 | Inflorescence diameter (observation) | Small<br>Medium<br>large | Medium (diagonal mean length including bracts = 7.4 cm.; mean width not including bracts = 5.3 cm) | Medium |
| 38 | Flower diameter (measurement) | Small<br>Medium<br>Large<br>Very large | Small | Small |
| 39 | Floret diameter (measurement) | Small<br>Medium<br>Large | Small | Small |
| 40 | Floret color (observation) | White<br>Yellowish white<br>Greenish yellow<br>Light Green<br>others | Yellow 150C | Greenish yellow 150C |
| 41 | Bract type (observation) | Single<br>Semi-double<br>Full-double<br>others | 83% are FUSED; 17% are Single (see Table 3) | Single and unfused |
| 42 | Uniformity of bract size (observation) | Not uniform<br>uniform | Not uniform | Uniform |
| 43 | Bract over-lapping (observation) | Not overlap<br>Slightly overlap<br>overlap | No overlap -- fused | Slightly overlap |
| 44 | Bract orientation (observation) | Ascending<br>Horizontal<br>arching | Recurved, Reflexed, or Flat | Horizontal |
| 45 | Bract rolling (observation) | Rolling inward<br>Horizontal<br>Rolling outward | Varies (may roll inward or outward | Horizontal |
| 46 | Degree of bract rolling (observation) | Weak<br>Medium<br>strong | strong | Weak |
| 47 | Bract curvature (observation) | In-curved<br>Horizontal<br>Out-curved | Varies (can be recurved, flat, or reflexed) | Horizontal |

TABLE 2-continued

Characteristics of Pam's Mountain Bouquet'
Color Descriptions are based upon the
Royal Horticultural Society's (RHS) colour chart, 2001.

| | Character | Generalized Characteristics | 'Pam's Mountain Bouquet' | Comparative Variety (Milky Way Select) |
|---|---|---|---|---|
| 48 | Bract twisting (observation) | None<br>Weak<br>Medium<br>strong | None | None |
| 49 | Whole shape of bracts (observation) | Oblong<br>Elliptical<br>Ovate<br>Obovate<br>Orbicular<br>others | Obovate<br>Ovate | |
| 50 | Shape of bract apex (observation) | Acuminate<br>Acute<br>Abtuse<br>Rotundate<br>Emarginated<br>others | Acuminate<br>Acuminate | |
| 51 | Bract length (measurement) | Short<br>Medium<br>Long | Medium | Medium |
| 52 | Bract width (measurement) | Narrow<br>Medium<br>wide | FUSED | Medium |
| 53 | Number of bracts (measurement) | Few<br>Medium(4)<br>Many(over 10) | FUSED, but 4 | Medium(4) |
| 54 | Bract color (measurement) | (color of bract in full bloom) | 155A (immature: 157A) | 155A |
| 55 | Bract variegation (observation) | Not variegated<br>variegated | Not variegated | Not variegated |
| 56 | Variegation pattern (observation) | Margined<br>Splashed<br>Bi-colored<br>Spotted<br>shaded<br>others | NA | NA |
| 57 | Variegation color (measurement) | (Color of variegation pattern of a bract in full bloom) | NA | NA |
| 58 | Pistil color (observation) | White<br>Yellowish white<br>Greenish white<br>Yellow green<br>Green<br>others | Yellow green<br>Not coded | Yellow green<br>Not coded |
| 59 | Stigma color (observation) | White<br>Yellowish white<br>Greenish white<br>Yellow green<br>Green<br>others | Dark Green (Not Coded) | Green (Not Coded) |
| 60 | Peduncle thickness (measurement) | Thin<br>Medium<br>thick | Medium | Medium |
| 61 | Peduncle length (measurement) | Short<br>Medium<br>long | Long (mean of 6.8 cm) | Medium |
| 62 | Peduncle color (observation) | Yellowish white<br>yellow<br>Yellow green<br>Green<br>Crimson<br>brown<br>others | Yellow green 144B | Yellow green 144B |

TABLE 2-continued

Characteristics of Pam's Mountain Bouquet'
Color Descriptions are based upon the
Royal Horticultural Society's (RHS) colour chart, 2001.

| Character | Generalized Characteristics | 'Pam's Mountain Bouquet' | Comparative Variety (Milky Way Select) |
|---|---|---|---|
| 63 Fruit shape (observation) | Elliptical<br>Ovate<br>Obovate<br>Globose<br>others | Globose | Globose |
| 64 Fruit length (measurement) | Short<br>Medium<br>long | Medium (about 4 cm) | Medium |
| 65 Fruit width (measurement) | Narrow<br>Medium<br>wide | Medium (about 4 cm) | Medium |
| 66 Fruit color (observation) | Yellow<br>Orange<br>Crimson<br>Purplish black<br>Black<br>others | Unripe:143B; Ripe 33B to 43A. Highly variable depending on ripeness | Ripe: 33B to 44A Highly variable depending on ripeness |
| 67 Fragrance (observation) | Absent<br>present | Absent | Absent |
| 68 Seed fertility (observation) | Sterile<br>Low<br>Medium<br>high | High | High |
| 69 Time to the first flowering (observation) | Early<br>Medium<br>late | Medium (April-mid-May) | Medium |
| 70 Blooming habit (observation) | Few<br>Medium<br>many | Many | Many |
| 71 Flowering season (observation) | One season flowering<br>Recurrent blooming<br>others | One season flowering | One season flowering |
| 72 Flowering time (observation) | Early<br>Medium<br>late | Medium | Medium |
| 73 Deciduous or evergreen (observation) | Deciduous<br>Half-deciduous<br>evergreen | Deciduous | Deciduous |
| 74 Cold hardiness (observation) | Weak<br>Medium<br>strong | Medium (to −20° C.—no effect) | Medium |
| 75 Heat tolerance (observation) | Weak<br>Medium<br>strong | Strong (to 40° C.—no effect) | Strong |
| 76 Pest resistance (observation) | Weak<br>Medium<br>strong | Strong (no specific pests noted; resistant to dogwood anthracnose and powdery mildew) | Strong |
| 77 Disease resistance (observation) | Weak<br>Medium<br>strong | Strong | Strong |
| 78 | | | |
| 79 Bark color | n/a | Grayed-Green 198B | Not observed |
| 80 Bark texture | n/a | Smooth | Not observed |
| 81 Angle of Emerging Branches | n/a | 20°-30° from vertical stem | Not observed |
| 82 Time to first leaf bud burst | n/a | Mid- to late-April | Not observed |
| 83 Leaf Vein color | n/a | Green-Greyed 192A | Not observed |

TABLE 2-continued

Characteristics of Pam's Mountain Bouquet'
Color Descriptions are based upon the
Royal Horticultural Society's (RHS) colour chart, 2001.

| Character | Generalized Characteristics | 'Pam's Mountain Bouquet' | Comparative Variety (Milky Way Select) |
|---|---|---|---|
| 84 Immature Leaf color | n/a | Similar to fully expanded leaf color | Not observed |
| 85 Bract base | n/a | Truncate | Not observed |
| 86 Bract margin | n/a | Entire | Not observed |
| 87 Vestiture | n/a | Puberulous, reticulate | Not observed |
| 88 Flower/ inflorescensce number | n/a | Mean = 34 | Not observed |
| 89 Seed shape | n/a | Flattened along length | Not observed |
| 90 Seed color | n/a | Greyed Yellow 162D | Not observed |
| 91 Seed number | n/a | 0-17 per fruit | Not observed |
| 92 Bloom duration | n/a | 3-5 weeks (dried, dead bracts are retained as a "collar" on peduncle until fruit fall in Autumn) | Not observed |
| 93 Time of Fruit Ripening | n/a | Begins mid- to late-August through October | Not observed |
| 94 Trunk diameter (at approximately breast height) | n/a | 18 cm at 15 years of age | Not observed |
| 95 Anther color | n/a | Greyed-purple N186 | Not observed |
| 96 Flower petal color | n/a | Yellow-green 145C | Not observed |
| 97 Style/Stigma description | n/a | Inconspicuous | Not observed |

Botanical classification: *Cornus kousa* 'Pam's Mountain Bouquet'.

Unique features: This tree features heavy flowering and exhibits fused bracts. About 82% of all bracts on the cultivar exhibit some degree of fusion (one side, two sides or three to four sides being fused; see data in Table 3).

TABLE 3

Cornus kousa 'Pam's Mountain Bouquet'
bract characteristics.

| Year | Not fused | One side fused | Two sides fused | 3-4 sides fused |
|---|---|---|---|---|
| 2008 (n = 50) | 7 (14%) | 3 (6%) | 12 (24%) | 28 (56%) |
| 2009 (n = 50) | 10 (20%) | 1 (2%) | 4 (8%) | 35 (70%) |
| 2011 (n = 50) | 9 (18%) | 5 (10%) | 9 (18%) | 27 (54%) |
| Mean | 9 (18%) | 3 (6%) | 8 (16%) | 30 (60%) |

All categories of fused bracts=82%.

Disease susceptibility: None noted. Powdery mildew caused by *Erisphe pulchra* and dogwood anthracnose *Discula destructiva* were not observed. Nearby *C. florida* (flowering dogwood) trees were heavily infested with powdery mildew, but not dogwood anthracnose.

Insect damage: None noted.

REFERENCES

Auge, R. M., M. T. Windham, J. L. Moore, W. T. Witte, E. Kubikova, W. E. Klingeman, R. M. Evans, J. H. Reiss, P. C. Flanagan, and A. M. Saxton. 2002. Leaf curl and water relations of *kousa* dogwoods showing resistance to summer stress. J. Environ. Hort. 20 (3):143-147.

Wadl, P. A., X. Wang, A. N. Trigiano, J. A. Skinner, M. T. Windham, T. A. Rinehart, S. M. Reed, V. R. Pantalone and R N. Trigiano. 2008. Molecular identification key for cultivars and lines of *Cornus florida* and *C. kousa* based on microsatellite loci. J. Amer. Soc. Hort. Sci. 133 (6): 783-793.

Wadl, P. W., X. Wang, B. E. Scheffler, T. A. Rinehart, and R. N. Trigiano. 2008. Microsatellites from *kousa* dogwood (*Cornus kousa*). Molec. Ecol. Res. 8:780-782. DOI: 10.1111/j.1471-8286.2007.0262.x.

Wadl, P. W., Windham, M. T., Evans, R., Trigiano, R. N. 2014. Three New Cultivars of *Cornus kousa*: Empire, Pam's Mountain Bouquet, and Red Steeple. HortScience 49 (9): 1230-1233.

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: Primer sequence

<400> SEQUENCE: 1

gcatttgtcc tttgtttgac at                                              22


<210> SEQ ID NO 2
<211> LENGTH: 22
<212> TYPE: DNA
<213> ORGANISM: Artificial Sequence
<220> FEATURE:
<223> OTHER INFORMATION: Primer sequence

<400> SEQUENCE: 2

tttttcgcga agtgttctct ac                                              22


<210> SEQ ID NO 3
<211> LENGTH: 23
<212> TYPE: DNA
<213> ORGANISM: Artificial Sequence
<220> FEATURE:
<223> OTHER INFORMATION: Primer sequence

<400> SEQUENCE: 3

gagcccagaa gaagaatata gac                                             23


<210> SEQ ID NO 4
<211> LENGTH: 21
<212> TYPE: DNA
<213> ORGANISM: Artificial Sequence
<220> FEATURE:
<223> OTHER INFORMATION: Primer sequence

<400> SEQUENCE: 4

atataattgg gttgggtttt g                                               21


<210> SEQ ID NO 5
<211> LENGTH: 24
<212> TYPE: DNA
<213> ORGANISM: Artificial Sequence
<220> FEATURE:
<223> OTHER INFORMATION: Primer sequence

<400> SEQUENCE: 5

gtcaaatttt tgatctttct ctct                                            24
```

-continued

<210> SEQ ID NO 6
<211> LENGTH: 24
<212> TYPE: DNA
<213> ORGANISM: Artificial Sequence
<220> FEATURE:
<223> OTHER INFORMATION: Primer sequence

<400> SEQUENCE: 6 ggagagacag agtacagtag aggt 24

<210> SEQ ID NO 7
<211> LENGTH: 24
<212> TYPE: DNA
<213> ORGANISM: Artificial Sequence
<220> FEATURE:
<223> OTHER INFORMATION: Primer sequence

<400> SEQUENCE: 7 aatttaggtt aaggttttga tttg 24

<210> SEQ ID NO 8
<211> LENGTH: 24
<212> TYPE: DNA
<213> ORGANISM: Artificial Sequence
<220> FEATURE:
<223> OTHER INFORMATION: Primer sequence

<400> SEQUENCE: 8 agagagaata ggttacagca tcat 24

<210> SEQ ID NO 9
<211> LENGTH: 22
<212> TYPE: DNA
<213> ORGANISM: Artificial Sequence
<220> FEATURE:
<223> OTHER INFORMATION: Primer sequence

<400> SEQUENCE: 9 tgtcactgct tacagaaaca at 22

<210> SEQ ID NO 10
<211> LENGTH: 24
<212> TYPE: DNA
<213> ORGANISM: Artificial Sequence
<220> FEATURE:
<223> OTHER INFORMATION: Primer sequence

<400> SEQUENCE: 10 tatgacgaga ttgtataagt tgct 24

<210> SEQ ID NO 11
<211> LENGTH: 23
<212> TYPE: DNA
<213> ORGANISM: Artificial Sequence
<220> FEATURE:
<223> OTHER INFORMATION: Primer sequence

<400> SEQUENCE: 11 ccaagtcagt ttggtagtaa ttc 23

<210> SEQ ID NO 12
<211> LENGTH: 23
<212> TYPE: DNA
<213> ORGANISM: Artificial Sequence
<220> FEATURE:
<223> OTHER INFORMATION: Primer sequence -continued

<400> SEQUENCE: 12 agtgcaactt ttacttgcta tgt 23

<210> SEQ ID NO 13
<211> LENGTH: 24
<212> TYPE: DNA
<213> ORGANISM: Artificial Sequence
<220> FEATURE:
<223> OTHER INFORMATION: Primer sequence

<400> SEQUENCE: 13 accaaccaaa agaagtataa agaa 24

<210> SEQ ID NO 14
<211> LENGTH: 24
<212> TYPE: DNA
<213> ORGANISM: Artificial Sequence
<220> FEATURE:
<223> OTHER INFORMATION: Primer sequence

<400> SEQUENCE: 14 cctataaata aggagtgatt tggt 24

<210> SEQ ID NO 15
<211> LENGTH: 24
<212> TYPE: DNA
<213> ORGANISM: Artificial Sequence
<220> FEATURE:
<223> OTHER INFORMATION: Primer sequence

<400> SEQUENCE: 15 cttaagtcac aaagacaatg aaat 24

<210> SEQ ID NO 16
<211> LENGTH: 24
<212> TYPE: DNA
<213> ORGANISM: Artificial Sequence
<220> FEATURE:
<223> OTHER INFORMATION: Primer sequence

<400> SEQUENCE: 16 aagagagttc agatttatct ttgc 24

<210> SEQ ID NO 17
<211> LENGTH: 23
<212> TYPE: DNA
<213> ORGANISM: Artificial Sequence
<220> FEATURE:
<223> OTHER INFORMATION: Primer sequence

<400> SEQUENCE: 17 cttttctaca cccttaacaa gtg 23

<210> SEQ ID NO 18
<211> LENGTH: 24
<212> TYPE: DNA
<213> ORGANISM: Artificial Sequence
<220> FEATURE:
<223> OTHER INFORMATION: Primer sequence

<400> SEQUENCE: 18 tagacaatat gtgcttaatt ggtt 24

-continued

```
<210> SEQ ID NO 19
<211> LENGTH: 20
<212> TYPE: DNA
<213> ORGANISM: Artificial Sequence
<220> FEATURE:
<223> OTHER INFORMATION: Primer sequence

<400> SEQUENCE: 19

ctgctcggtt aaggtatgtt                                                20


<210> SEQ ID NO 20
<211> LENGTH: 25
<212> TYPE: DNA
<213> ORGANISM: Artificial Sequence
<220> FEATURE:
<223> OTHER INFORMATION: Primer sequence

<400> SEQUENCE: 20

tttaaagtgc gttgtataca taaat                                          25


<210> SEQ ID NO 21
<211> LENGTH: 20
<212> TYPE: DNA
<213> ORGANISM: Artificial Sequence
<220> FEATURE:
<223> OTHER INFORMATION: Primer sequence

<400> SEQUENCE: 21

agcactcata gtccttgcac                                                20


<210> SEQ ID NO 22
<211> LENGTH: 24
<212> TYPE: DNA
<213> ORGANISM: Artificial Sequence
<220> FEATURE:
<223> OTHER INFORMATION: Primer sequence

<400> SEQUENCE: 22

gttaaaacga agaagataca acaa                                           24
```

We claim:

1. A new and distinct cultivar of Dogwood tree, *Cornus kousa*, named 'PAM'S MOUNTAIN BOUQUET', as illustrated and described.

* * * * *

UNITED STATES PATENT AND TRADEMARK OFFICE

CERTIFICATE OF CORRECTION

PATENT NO. : PP25,575 P3
APPLICATION NO. : 13/506624
DATED : May 26, 2015
INVENTOR(S) : Trigiano et al.

It is certified that error appears in the above-identified patent and that said Letters Patent is hereby corrected as shown below:

In the specification

Column 4,
Line 21, "Characteristics of Pam's Mountain Bouquet'" should read
--Characteristics of 'Pam's Mountain Bouquet'--.

Column 8,
Lines 13-14,

| | | | | |
|---|---|---|---|---|
| "49 | Whole shape of bracts | Oblong Elliptical | Obovate Ovate" | |

should read

| | | | | |
|---|---|---|---|---|
| --49 | Whole shape of bracts | Oblong Elliptical | Ovate | Obovate--. |

Lines 17-18,

| | | | | |
|---|---|---|---|---|
| "50 | Shape of bract apex | Acuminate Acute | Acuminate Acuminate" | |

should read

| | | | | |
|---|---|---|---|---|
| --50 | Shape of bract apex | Acuminate Acute | Acuminate | Acuminate--. |

Signed and Sealed this
Thirteenth Day of October, 2015

Michelle K. Lee

Michelle K. Lee
*Director of the United States Patent and Trademark Office*